United States Patent [19]

Toller

[11] Patent Number: 5,342,388
[45] Date of Patent: Aug. 30, 1994

[54] METHOD AND APPARATUS FOR SEALING LUMINAL TISSUE

[76] Inventor: Sonia Toller, 4732 Hollyberry Dr., Orlando, Fla. 32812

[21] Appl. No.: 37,073

[22] Filed: Mar. 25, 1993

[51] Int. Cl.⁵ .................................................. A61B 17/12
[52] U.S. Cl. .................................. 606/201; 601/134
[58] Field of Search ............ 606/1, 79, 160, 201-204, 606/204.35; 128/57, 62 R, 67, 60; 100/299; 81/486, 488, 489; 452/141, 146

[56] References Cited

U.S. PATENT DOCUMENTS

| | | | |
|---|---|---|---|
| 1,050,836 | 1/1913 | Jones | 128/60 |
| 1,965,861 | 7/1934 | Schneider | 128/67 |
| 2,754,825 | 7/1956 | Richmond | 606/203 |
| 3,017,879 | 1/1962 | Sapit et al. | 604/1 |
| 3,228,392 | 1/1966 | Speyer | 128/60 |
| 3,411,505 | 11/1968 | Nobis | 606/201 |
| 3,774,614 | 11/1973 | Cook | 606/201 |
| 3,779,249 | 12/1973 | Semler | 606/201 |
| 3,980,079 | 9/1976 | Brodbeck | 128/57 |
| 4,233,980 | 11/1980 | McRae et al. | 606/201 |
| 4,358,142 | 11/1982 | Montalvo | 100/299 |
| 4,572,182 | 2/1986 | Royse | 606/201 |
| 4,599,779 | 7/1986 | Thibault | 81/488 |
| 4,610,248 | 9/1986 | Rosenberg | 606/201 |
| 4,793,363 | 12/1988 | Ausherman | 606/79 |
| 5,133,734 | 7/1992 | Lee | 606/201 |
| 5,197,972 | 3/1993 | Hakki | 606/201 |

FOREIGN PATENT DOCUMENTS 9208411  5/1992  PCT Int'l Appl. ............... 606/201

OTHER PUBLICATIONS

Zimmer, *Journal of Bone and Joint Surgery,* Jul. 1952, p. 19.

*Primary Examiner*—Ralph Lewis
*Attorney, Agent, or Firm*—Steven C. Stewart; James H. Beusse

[57] ABSTRACT

A manual assist apparatus and method for obtaining hemostasis of a wound on luminal tissue, such as a femoral artery puncture, after a cannulated procedure such as angioplasty. This apparatus has a substantially cylindrically shaped handle with a rod extending downward into a sterile disposable disk member. The disk member is placed just above the catheter insertion site with catheter inside a notch of the disk member for proper pressure point for compression of artery, as the catheter is inside of the artery. The catheter is then removed from artery and pressure applied to the handle in downward direction to force the disk member to compress the artery for the purpose of controlling arterial bleeding and to obtain hemostasis. The weight of the cylindrically shaped handle assists the practitioner with above mentioned compression task. The disk member may then be discarded after use.

5 Claims, 1 Drawing Sheet

METHOD AND APPARATUS FOR SEALING LUMINAL TISSUE

BACKGROUND OF THE INVENTION

This invention relates to a method and apparatus for sealing luminal tissue, and more particularly, to obtaining hemostasis in the femoral groin after cannulation of the femoral artery for the purpose of heart catheterization or coronary angioplasty.

The femoral artery is a very high pressure artery which requires that direct pressure be applied above the puncture site for twenty to thirty minutes in order to guarantee that hemostasis (bleeding has stopped) is attained. For example, if an arterial sheath is removed from the femoral artery in the groin and no attempt to apply pressure is made, this patient would bleed to death in a matter of minutes.

To prevent this from happening, one must remain at the groin site holding very firm pressure with gloved hands directly above the puncture site for twenty to thirty minutes. As a result, fatigue, numbness, stiffness and pain occur in the fingers, hands, wrist and forearms of the practitioner performing this procedure. Also, there is the possibility that a glove could have or develop a tear, thereby allowing direct pressurized digital (fingers) contact with bodily fluids (blood). Extensive use of the procedure over a long period of time without the aid of any assist devices, can cause extensive injury to the user. One such injury is Carpal Tunnel Syndrome.

One possible solution for sealing arteries is described in U.S. Pat. No. 3,411,505. This device has a handle at one end and a rod at its other end which contacts internal arteries to be sealed.

A drawback to this device is that it is hard to balance on the artery when supported by hand and may tend to fall over. Another drawback is that the device requires excessive hand pressure to seal the wound, resulting in the wrist of the user becoming tired when pressure is applied for a long time. This device may also require sterilization after the procedure possibly requiring disposal of the device. Further, the device was not designed for internal use and may not be able to apply sufficient pressure to an artery when used externally.

SUMMARY OF THE INVENTION

An object of this invention is to provide an improved apparatus for closing luminal tissue.

Another object of the invention is to seal luminal tissue such as an artery or a vein with a hand held device that has sufficient weight to close the lumen without excessive hand pressure.

A further object of the invention is to close tissue with a device that is easy to balance over the tissue to be sealed.

An additional object of the invention is to provide a method of controlling blood flow after removing a catheter from an artery to permit the artery to seal itself with a device having a disposable portion that contacts the tissue.

These and other objects are provided with an apparatus for applying pressure to luminal tissue. The apparatus has an elongated substantially cylindrical sloped handle having a first and second end. An elongated rod extends outward from said handle between said first and second end. A disk is removably connected to said elongated rod at a distal end from said handle and adapted to rest on a body of a patient such that when pressure is applied to the handle, the disk depresses the luminal tissue. The apparatus is easy to use as it has no moving parts or adjustments other than snapping a new sterile disk on the apparatus for each new patient.

DESCRIPTION OF THE PREFERRED EMBODIMENTS

Figure 1:
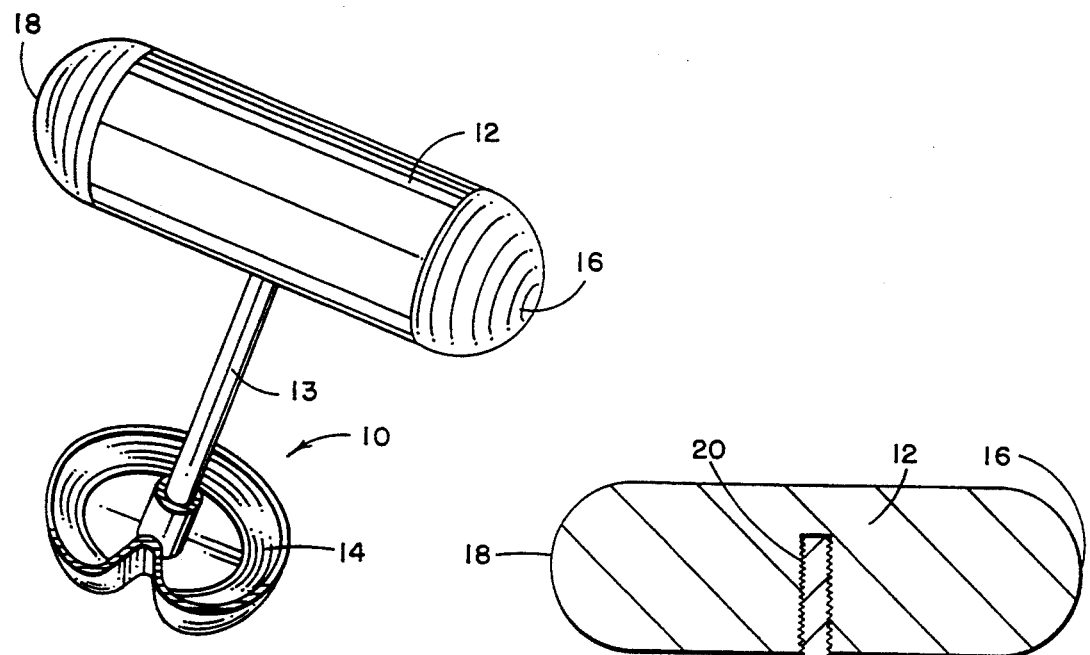
FIG. 1 is a perspective view of the invention.
Figure 2:
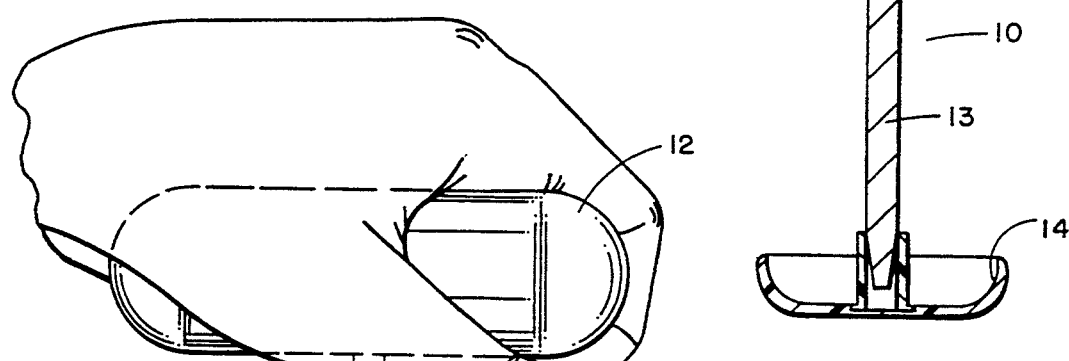
FIG. 2 is a side sectioned view of the invention shown in FIG. 1.
Figure 3:
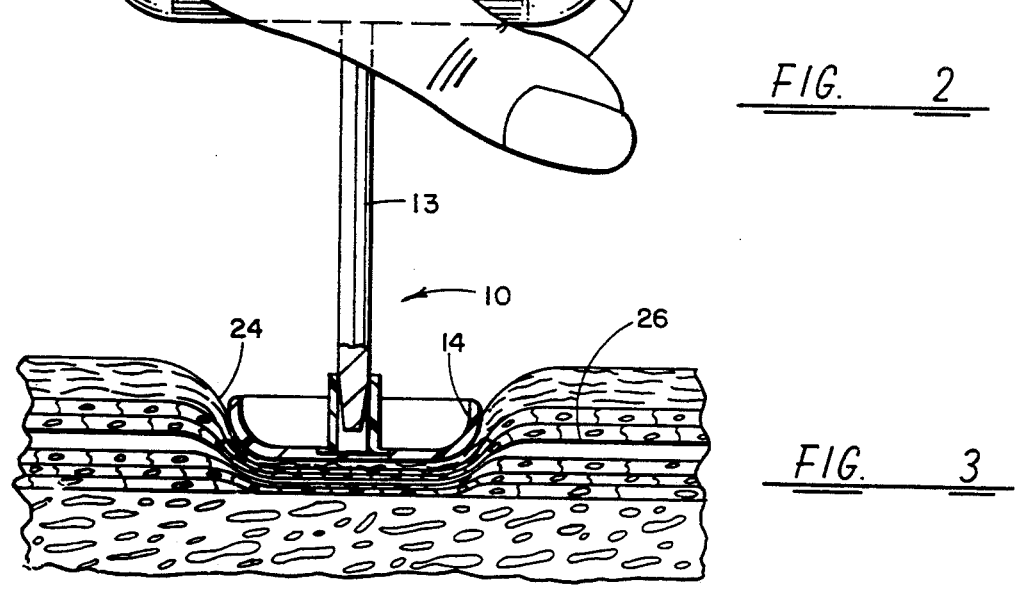
FIG. 3 is a partial side sectioned view of the invention closing an artery.

Referring to FIGS. 1-3 there is shown the invention designated generally by 10, having a substantially elongated and cylindrically shaped handle 12 connect with rod 13 to a sterile disk member 14. Preferably handle 12 and rod 13 are constructed from a surgical stainless steel material. The disk member 14 preferably has a flat bottom surface and is one constructed as disclosed in U.S. Pat. No. 4,572,182 which is herein incorporated by reference.

Handle 12 has a first end 16 and second end 18 with a threaded aperture 20 (FIG. 2) extending into handle 12 between ends 16 and 18. Handle 12 is preferably of sufficient size to weigh to at least partially close on artery. Typically handle 12 weighs about at least 1 pound. In some applications it may be preferable to have handle 12 to weigh greater than 1 pound.

Rod 18 is threaded at one end to screwably mate with the walls of aperture 20. Aperture 20 is positioned in handle 12 so that the threaded end of rod 18 extends through handle 12 center of gravity. Rod 18 extends perpendicularly outward from handle 14 to disk member 14. In this manner, handle 14 is balanced about rod 18 during use.

The other end 22 of rod is slightly tapered to snugly fit into disk member 14. The tapered end of rod 18 is press fit into member 14 so that it is held securely in place therein. Rod 18 is removable from disk member 14 after use to allow easy disposal of disk member 14.

Referring to FIG. 3, during an angioplasty or heart catheterization procedure disk member 14 is placed over the surface 24 of an artery of a patient. Invention 10 may be used in other application to seal other luminal tissue types when it is necessary to control fluid flow therethrough.

The hand of a person then applies downward pressure onto cylindrical handle 14. This pressure is then transferred through the rod 13 into the disk member 14 to, at least partially, close the artery 26. Preferably the weight of the handle 14 is sufficient to, at least partially, close the wound without any force by the user. Downward pressure is continually applied until the blood flowing through the artery forms as clot so the wound on the artery 26 can seal itself. Once the wound is closed, the apparatus 10 is removed from artery 26. The disk member 14 is then removed from the end of rod 13 and discarded.

On subsequent use a new sterile disk member 14 is press fit on the end of bar 13 allowing apparatus 10 to be used on another patient.

This concludes the description of the preferred embodiments. A reading by those skilled in the art will bring to mind various changes without departing from the spirit and scope of the invention. It is intended, however, that the invention only be limited by the following appended claims.

What is claimed is:

1. An apparatus for applying pressure to luminal tissue above a femoral artery puncture site after completion of a cannulated procedure, the apparatus comprising:
   an elongated substantially cylindrically shaped handle having a first and second end, said cylindrical handle weighing at least about one pound;
   an elongated rod extending outward from said handle between said first and second end; and
   a disk removably connected to said elongated rod at a distal end from said handle and adapted to rest on a body such that when pressure is applied to said handle, said disk depresses the luminal tissue, said disk including a notch extending from the periphery of the disk towards a center portion of said disk, said notch having its largest width at said periphery, said disk having a substantially flat bottom such that said handle can be supported in the upright position when said disk rests on a flat surface.

2. The apparatus as recited in claim 1 wherein said rod is substantially cylindrically shaped and extends into said handle and through a center of gravity of said handle between said first and second end.

3. The apparatus as recited in claim 1 wherein said handle has sufficient weight to close said femoral artery when said disk rests on said body.

4. The apparatus as recited in claim 1 wherein said handle weighs more than the disk.

5. The apparatus as recited in claim 1 wherein said rod is threaded at one end and is screwed into said handle.

* * * * *

UNITED STATES PATENT AND TRADEMARK OFFICE
CERTIFICATE OF CORRECTION

PATENT NO. : 5,342,388
DATED : August 30, 1994
INVENTOR(S) : Sonia Toller

It is certified that error appears in the above-identified patent and that said Letters Patent is hereby corrected as shown below:

> In column 1, line 43, the word "not" should be deleted.

Signed and Sealed this

Twentieth Day of December, 1994

Attest:

BRUCE LEHMAN

Attesting Officer     Commissioner of Patents and Trademarks